(12) United States Patent
Zhang

(10) Patent No.: US 9,277,956 B2
(45) Date of Patent: Mar. 8, 2016

(54) SYSTEM FOR AUTOMATIC MEDICAL ABLATION CONTROL

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 636 days.

(21) Appl. No.: 13/572,862

(22) Filed: Aug. 13, 2012

(65) Prior Publication Data

US 2013/0116681 A1 May 9, 2013

Related U.S. Application Data

(60) Provisional application No. 61/557,500, filed on Nov. 9, 2011.

(51) Int. Cl.
| | |
|---|---|
| A61B 18/00 | (2006.01) |
| A61B 18/12 | (2006.01) |
| A61B 18/14 | (2006.01) |
| A61B 19/00 | (2006.01) |

(52) U.S. Cl.
CPC ......... *A61B 18/1206* (2013.01); *A61B 18/1492* (2013.01); *A61B 19/50* (2013.01); *A61B 19/56* (2013.01); *A61B 2018/0075* (2013.01); *A61B 2018/00702* (2013.01); *A61B 2018/00761* (2013.01); *A61B 2018/00839* (2013.01); *A61B 2019/461* (2013.01); *A61B 2019/564* (2013.01); *A61B 2019/566* (2013.01)

(58) Field of Classification Search
CPC ................ A61B 18/1492; A61B 2018/00702; A61B 2018/00839; A61B 17/2202; A61B 17/320068; A61B 18/1206; A61B 18/1442; A61B 18/24; A61B 19/50; A61B 19/56; A61B 2017/00106; A61B 2017/00243; A61B 2017/003
USPC ................ 606/27, 34, 41; 607/4–5
See application file for complete search history.

(56) References Cited

U.S. PATENT DOCUMENTS

| | | | |
|---|---|---|---|
| 5,486,199 | A | 1/1996 | Kim et al. |
| 5,522,852 | A | 6/1996 | White et al. |
| 5,549,641 | A | 8/1996 | Ayers et al. |
| 5,683,429 | A | 11/1997 | Mehra |
| 5,788,717 | A | 8/1998 | Mann et al. |
| 5,843,133 | A | 12/1998 | Routh et al. |
| 5,853,426 | A | 12/1998 | Shieh |
| 5,968,079 | A | 10/1999 | Warman et al. |
| 6,064,906 | A | 5/2000 | Langberg et al. |

(Continued)

FOREIGN PATENT DOCUMENTS

WO WO2008007236 a2 1/2008

*Primary Examiner* — Rex R Holmes

(57) ABSTRACT

A system provides heart ablation unit control. The system includes an input processor for acquiring electrophysiological signal data from multiple tissue locations of a heart and data indicating tissue thickness at the multiple tissue locations. A signal processor processes the acquired electrophysiological signal data to identify location of particular tissue sites of the multiple tissue locations exhibiting electrical abnormality in the acquired electrophysiological signal data and determines an area of abnormal tissue associated with individual sites of the particular sites. An ablation controller automatically determines ablation pulse characteristics for use in ablating cardiac tissue at an individual site of the particular tissue sites in response to the acquired data indicating the thickness of tissue and determined area of abnormality of the individual site.

23 Claims, 11 Drawing Sheets

(56) References Cited

U.S. PATENT DOCUMENTS

| | | |
|---|---|---|
| 6,285,908 B1 | 9/2001 | Mann et al. |
| 6,490,479 B2 | 12/2002 | Bock |
| 6,597,943 B2 | 7/2003 | Taha et al. |
| RE38,515 E | 5/2004 | White |
| 6,937,887 B2 | 8/2005 | Bock |
| 6,968,226 B2 | 11/2005 | Mehra et al. |
| 7,142,912 B2 | 11/2006 | Wagner et al. |
| 7,153,301 B2 | 12/2006 | Swartz et al. |
| 7,177,682 B2 | 2/2007 | Lovett |
| 7,321,794 B2 | 1/2008 | Thacker et al. |
| 7,519,421 B2 | 4/2009 | Denker et al. |
| 7,590,449 B2 | 9/2009 | Mann et al. |
| 7,627,368 B2 | 12/2009 | Houben et al. |
| 7,634,310 B2 | 12/2009 | Lee et al. |
| 7,715,907 B2 | 5/2010 | Koertge et al. |
| 7,783,352 B1 | 8/2010 | Ryu et al. |
| 8,221,411 B2 | 7/2012 | Francischelli et al. |
| 2006/0253115 A1* | 11/2006 | Avitall et al. .................. 606/41 |
| 2009/0012412 A1 | 1/2009 | Wiesel |
| 2009/0216221 A1 | 8/2009 | Davis et al. |
| 2009/0270749 A1 | 10/2009 | Haluska |
| 2010/0023004 A1* | 1/2010 | Francischelli et al. ......... 606/41 |
| 2010/0268295 A1 | 10/2010 | Imran et al. |
| 2010/0280394 A1 | 11/2010 | Blomqvist |
| 2011/0028848 A1* | 2/2011 | Shaquer et al. ............... 600/463 |
| 2011/0106070 A1 | 5/2011 | Fischer et al. |
| 2011/0201900 A1 | 8/2011 | Zhang et al. |
| 2012/0143179 A1 | 6/2012 | Avitall |

* cited by examiner

FIGURE 2A

| Parameters for Ablation Control (203) | Functions and application (206) |
|---|---|
| 210 Ablation start time(trigger and synchronizing/gating timing) T1 | Surface ECG, intra-cardiac electrograms, hemodynamic pressure signals, SPO2 signals, vital signs, respiration, are used to trigger ablation start time for each ablation. Each ablation process are divided in one embodiment into multiple small gated cycles by ECG or other patient signal gating, which may be electrophysiologically more effective to terminate the abnormal AF rotors. |
| 212 Ablation frequency | The ablation electrical signal and pulse frequency are adaptively varied, such as 450K Hz, 500K Hz, the ablation frequency is dynamically and adaptively varied in response to physician setup or automatic detection and calculation of the abnormality. Different frequency ablation pulse types may be combined for treatment. |
| 214 Tissue wall thickness | Cardiac tissue and wall thickness may be varied and can be used to control the delivered ablation energy. This feature may be combined and utilized with function and ablation mapping and registration. |
| 216 Ablation effective area (depending on catheter to tissue pressure) | Different ablation frequency, ablation pulse mode, ablation energy, affect the area of the tissue undergoing ablation shock. Ablation effective area provides a threshold for the safe treatment of a patient. |
| 218 Registration and mapping of EP functions, to potential ablation points | Different parameters are presented in an image and used for automatic closed loop ablation and diagnosis. The registration mapping provides an ablation sequence, priority, severity, with user friendly visualization and UI interface. |
| 220 Ablation sequence and priority list | Usually in AF treatment, there may be multiple abnormal rotors and pathological sites. Ablation sequence and priority mapping and registration are identified and displayed to a physician. This method is usable with a catheter position and heart navigation system, |

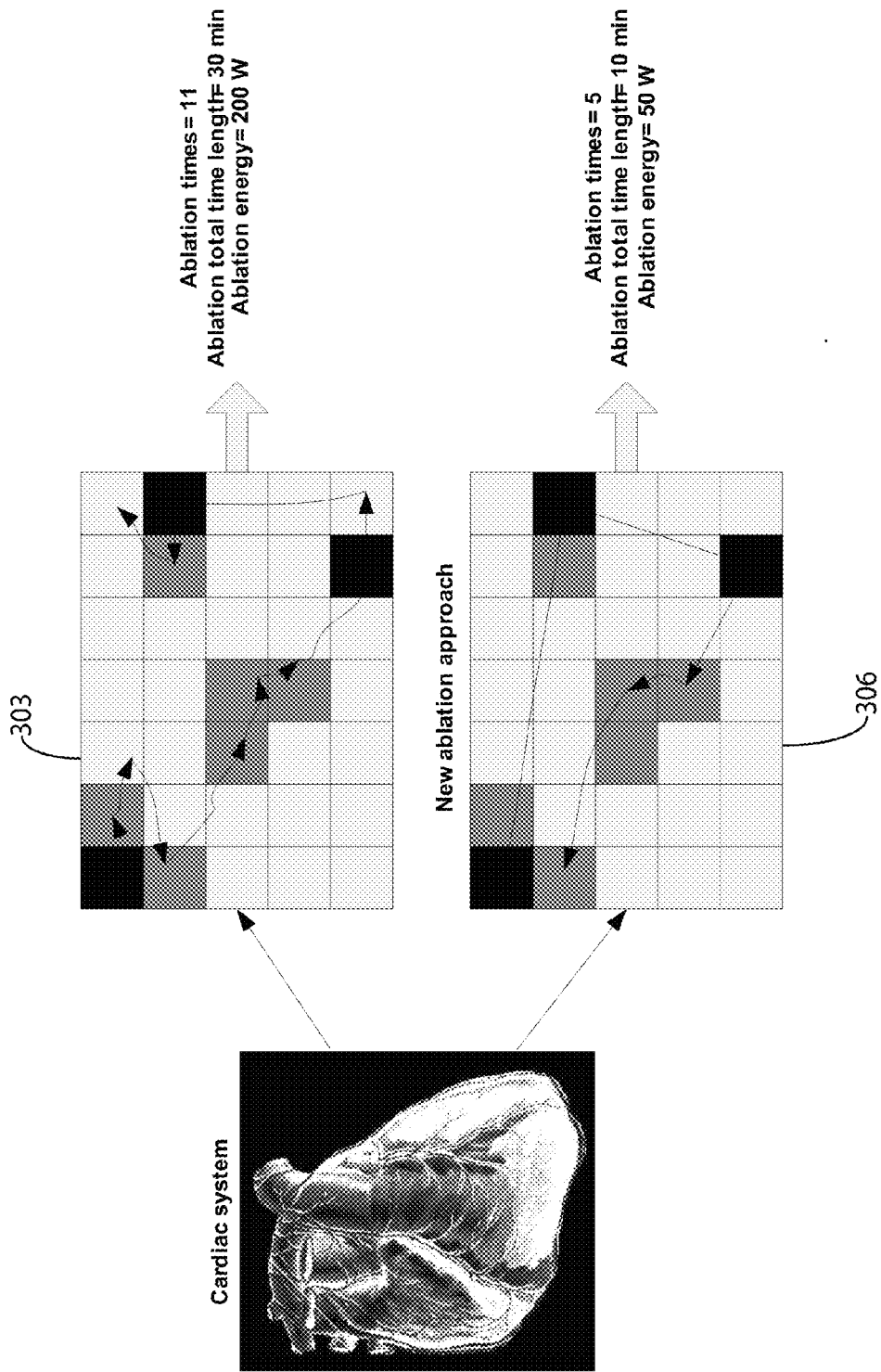

Figure 7a
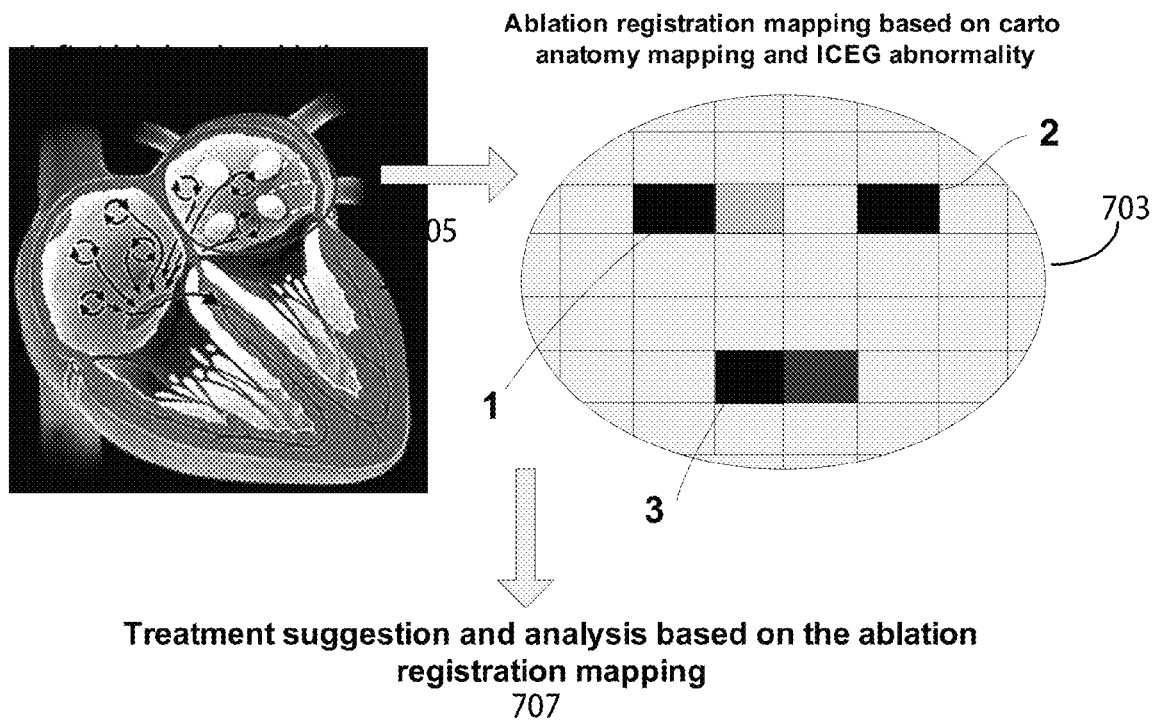
Ablation registration mapping based on carto anatomy mapping and ICEG abnormality
Treatment suggestion and analysis based on the ablation registration mapping
707
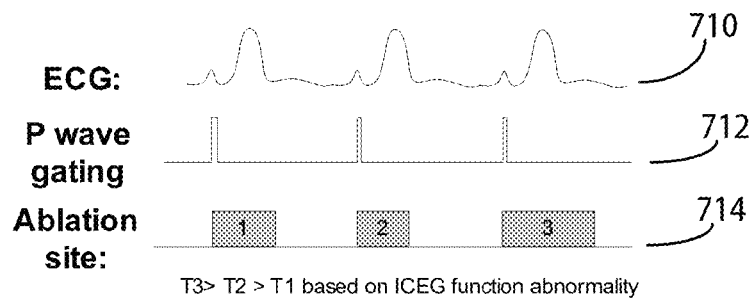
T3 > T2 > T1 based on ICEG function abnormality
Figure 7b

FIGURE 8

| Size of abnormal tissue | Tissue thickness | Ablation times – pulse width | Ablation duration for each ablation |
|---|---|---|---|
| Small size (such as area 2 in the example) | Thickness 1 | once | T2 |
| Middle size (such as area 1 in the example) | Thickness 2 | twice | T1 |
| bigger size (such as area 3 in the example) | Thickness 3 | Three times | T3 |

Figure 9

| | |
|---|---|
| Dominant frequency in the P wave (825) | Ablation frequency control (827) |
| Area 1 P wave signal is 20 Hz | 474 K Hz |
| Area 2 P wave signal is 16 Hz | 450 Hz |
| Area 3 P wave signal is 25 Hz | 500 Hz |

(823)

| | |
|---|---|
| AF rotor characteristics for each area (845) | Ablation frequency control (847) |
| Single phase rotor | Uniphasic ablation pulse |
| Biphasic rotor | Biphasic ablation pulse |
| Single phase rotor | Uniphasic ablation pulse |

SYSTEM FOR AUTOMATIC MEDICAL ABLATION CONTROL

This is a non-provisional application of provisional application Ser. No. 61/557,500 filed Nov. 9, 2011, by H. Zhang.

FIELD OF THE INVENTION

This invention concerns a system for heart ablation unit control by automatically determining ablation pulse characteristics for use in ablating cardiac tissue at an individual tissue site in response to acquired data indicating the thickness of tissue and determined area of abnormality of the individual site.

BACKGROUND OF THE INVENTION

Atrial fibrillation (AF) is one of most common cardiac rhythm disorders and irregularities of cardiac patients. Usually, surface ECG signal analysis based on waveform morphology and time domain parameters is utilized for cardiac arrhythmia detection by P wave signal characterization, for example. Known invasive catheter based ablation is used for treating and terminating atrial functional arrhythmias and electrophysiological disorders, especially atrial fibrillation and flutters. However, known clinical ablation and treatment procedures are based on physician subjective estimation and require extensive clinical knowledge and electrophysiological experience. There is a lack of an efficient and effective ablation control system for ablation parameter setting and adjustment, such as for control of duration of ablation shock signals, ablation energy, ablation pulse pattern and ablation site priority. There is also a lack of a system providing qualitative and quantitative characterization of atrial fibrillation, especially for quantification of severity of AF.

Usually, surface ECG signal analysis based on waveform morphology and time domain parameters is utilized for cardiac AF rhythm detection and characterization. Such waveform morphology includes P wave morphology changes, R-R wave time interval, and heart rate variability. However, known waveform morphology and time domain parameter analysis is often subjective and time-consuming, and requires extensive expertise and clinical experience for accurate pathology interpretation and proper cardiac rhythm management. Some known recent research has applied mathematical theories to biomedical signal interpretation, such as, frequency analysis (such as dominant frequency analysis), wavelet decomposition analysis, statistical analysis (such as autocorrelation analysis, coherence analysis), and nonlinear entropy evaluation. Nevertheless, this research is focused on generating a pathology index for qualitative cardiac AF rhythm identification. Know methods for atrial pathology and malfunction diagnosis and interpretation typically focus on qualitative electrical pulse conduction and excitation progression in an atrial chamber and tissue. There is a lack of a system able to identify atrial arrhythmia area size and severity for ablation treatment quantitatively, such as for an atrial fibrillation site in the right and left atrial chambers.

Known systems track and navigate atrial chamber size, myocardial wall thickness, tissue electrical impedance and atrial contraction mode but fail to comprehensively determine atrial arrhythmia treatment including ablation energy and pulse pattern selection. Known ablation machines and electrical treatment medical devices utilize continuous ablation shock signals for burning and terminating abnormal tissue function, such as pathological atrial fibrillation rotors in atrial chamber tissue but fail to comprehensively modulate ablation energy pulses by adaptively adjusting ablation parameters during electrical treatment including electrical pulse length, energy and ablation time length. A system according to invention principles addresses these deficiencies and associated problems.

SUMMARY OF THE INVENTION

A system detects and characterizes atrial signals (including surface ECG signals, intra-cardiac electrograms, invasive or non-invasive atrial hemodynamic signals) to provide an accurate event time, atrial arrhythmia type, abnormal excitation rotor location and severity in the treatment of atrial fibrillation arrhythmia. A system provides heart ablation unit control. The system includes an input processor for acquiring electrophysiological signal data from multiple tissue locations of a heart and data indicating tissue thickness at the multiple tissue locations. A signal processor processes the acquired electrophysiological signal data to identify location of particular tissue sites of the multiple tissue locations exhibiting electrical abnormality in the acquired electrophysiological signal data and determines an area of abnormal tissue associated with individual sites of the particular sites. An ablation controller automatically determines ablation pulse characteristics for use in ablating cardiac tissue at an individual site of the particular tissue sites in response to the acquired data indicating the thickness of tissue and determined area of abnormality of the individual site.

BRIEF DESCRIPTION OF THE DRAWING

FIGS. 2A and 2B show a Table identifying ablation control parameters and indicating their functions, according to invention principles.

FIG. 3 illustrates comparison of a known ablation system with an ablation system according to invention principles.

FIGS. 7a and 7b show a multi-functional ablation registration map and an associated ablation pulse sequence, according to invention principles.

FIGS. 8, 9 and 10 present lookup tables showing tissue abnormality and rotor characteristics and associated ablation control parameters, according to invention principles.

DETAILED DESCRIPTION OF THE INVENTION

Figure 1:
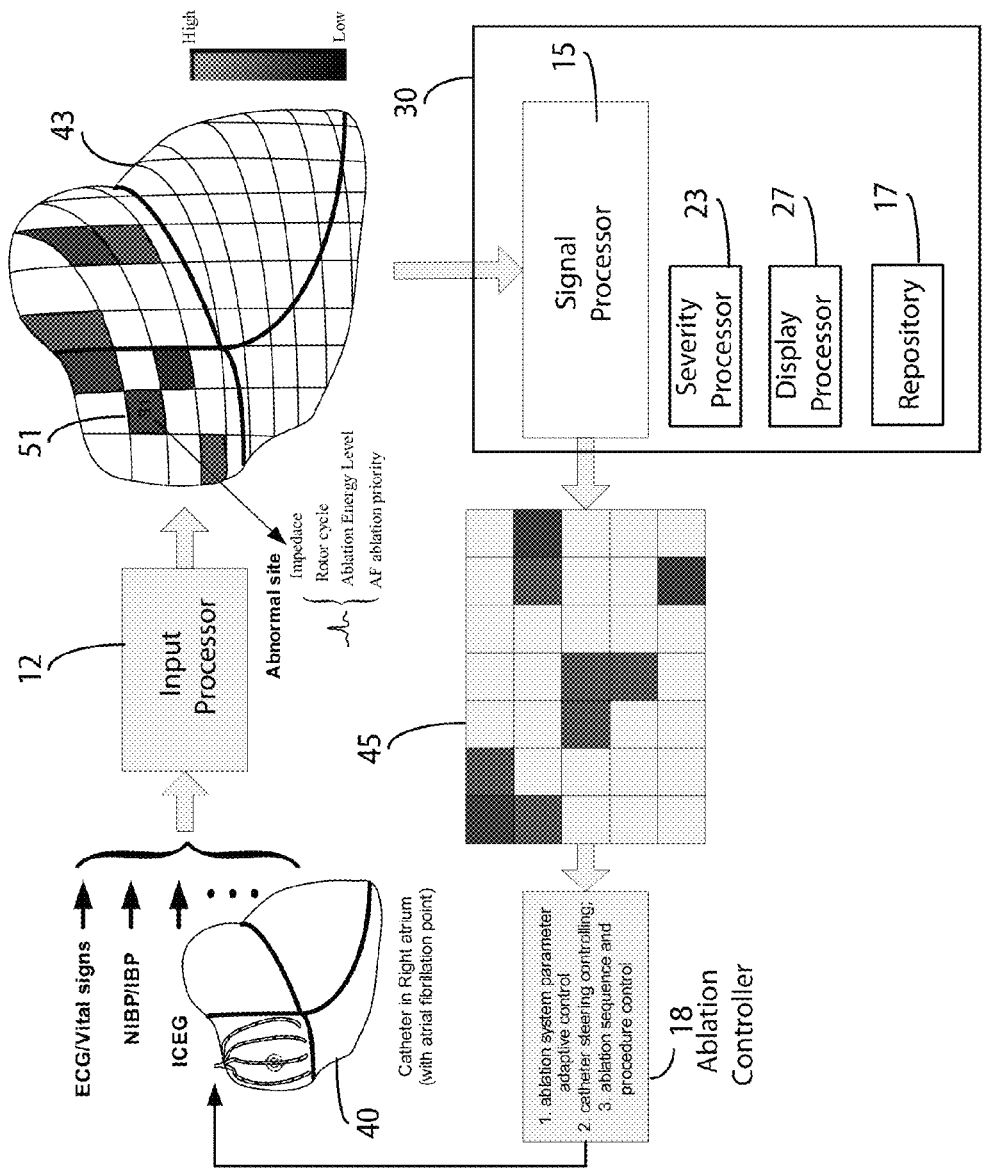
FIG. 1 shows a system for heart ablation unit control, according to invention principles.

A system improves analysis and interpretation of cardiac atrial electrophysiological activities for atrial pathology diagnosis and treatment, by detecting and characterizing atrial signals (including surface ECG signals, intra-cardiac electrograms, invasive or non-invasive atrial hemodynamic signals) in response to an atrial gating signal derived from a P wave signal or atrial function portion. The gating or synchronization signal is derived by electrical or feedback-loop control based on cardiac measurements and derived parameters from ECG signals, hemodynamic pressure signals, SPO2 signals including P wave start time, P wave peak time, dP/dt (rate of pressure change), frequency and energy waveform peak time. The system is utilized to identify, quantify and map signal waveform changes and distortions within atrial function signals with registration of anatomical cardiac tissue and characterizes atrial multi-rotor (multi-excitation) signal patterns and determines ablation treatment parameters. The system provides an accurate event time, atrial arrhythmia type, abnormal excitation rotor location and severity, atrial ablation mode, such as appropriate shock energy and ablation sequence/priority in the treatment of the atrial fibrillation arrhythmia.

Known ablation methods for atrial fibrillation typically apply electrical shock energy and deliver electrical signals to cardiac tissue without gating electrical ablation signals and lack synchronization control. Known systems fail to provide adaptive electrical shock treatment and location mapping including adaptively varying ablation energy, ablation sequence and ablation priority. Known systems also fail to provide automatic ablation catheter steering in an automatic or robot based EP and Ablation catheter control system. Know cardiac image methods in an operating room (OR) focus on catheter insertion, stent installation and blood flow monitoring. However a cardiac chamber and vessel are not rigid tissue, but soft tissue, which has a contraction and reperfusion mode and known systems typically fail to use this information for diagnosis of cardiac soft tissue characteristics. The inventor has identified a need for a gating system for catheter movement based ablation control and for AF ablation with reduced noise sensitivity.

The system employs a signal gating and synchronization method for atrial function mapping for AF analysis and ablation estimation that is also applicable to other portions of a cardiac electrophysiological signal. The system is used to monitor and diagnose pathologies and malfunctions of a heart and circulation system during cardiac arrhythmias using cardiac arrhythmia mapping, severity evaluation and discrimination of different cardiac pathological rhythms including atrial tachycardia and ventricle arrhythmias, for example.

The system provides intelligent automatically adaptive ablation control of ablation energy, non-continuous ablation pulse sequences, tissue location mapping and registration. The system quantitatively and qualitatively characterizes patient cardiac (tissue and rhythm) atrial arrhythmias using advantageous parameters and control methods and provides atrial fibrillation anatomical navigation, function synchronization, tissue ablation location mapping and registration. The system provides treatment of atrial abnormality based on atrial signal function gating and mapping, identifies atrial tissue and rhythm disorders, differentiates between cardiac arrhythmias, characterizes pathological severity, predicts life-threatening events, and supports evaluation of administered medications. The system may be utilized in other cardiac arrhythmia detection and characterization, such as of myocardial ischemia, ventricular tachycardia, and ventricular fibrillation.

There are different known ablation devices including electrical and optical devices for which a user determines specific parameters for ablation control, such as ablation energy and ablation duration. These parameters require a user to have extensive electrophysiological knowledge and clinical experience. Some ICD (implantable cardiac device) systems can perform specific ablation and electrical shock based on specific calculations but are susceptible to false alarms causing unnecessary false ablation and a substantial safety risk. In contrast, the system advantageously provides a closed loop system with substantially optimum parameters to avoid over burning and unwanted ablation by using atrial information and adaptive ablation control using non-continuous ablation with adjustable ablation pulse characteristics and duration, for example. Advantageous ablation control parameters are generated and used for ablation pattern control, which increases usability, reliability and efficiency of an ablation device.

Known systems typically display ablation application related parameters including, temperature (for monitoring an ablation tip), tissue impedance (for monitoring ablation effectiveness), ablation energy (for controlling delivered energy to cardiac tissue) and time duration (for controlling maximum ablation time duration for each ablation procedure). In contrast, the system provides ablation severity and priority based on registration of cardiac anatomical navigation data and intra-cardiac signal function location.

FIG. 1 shows system 10 for heart ablation unit control using closed loop automatic ablation selection and determination for real time adaptive ablation parameter control. Input processor 12 continuously acquires patient signals (including ablation related intra-cardiac electrograms, surface ECG, NIBP/IBP, vital signs) from a patient and heart 40. Processor 12 acquires electrophysiological signal data from multiple tissue locations of a heart and data indicating tissue thickness at the tissue locations The invasive and ICEG data and signals are associated (mapped) to corresponding tissue locations indicated in a predetermined anatomical 2D or 3D image 43. The signal information and predetermined ablation points, are dynamically mapped into a registered ablation image 43. Ablation image 43 identifies tissue locations that are associated with calculated parameters to provide a visualization of function, anatomy and treatment concurrently to facilitate adaptive automatic ablation system control and ablation procedure optimization. The parameters include sequence of ablation, ablation time, energy for each ablation point, minimization of treatment time, optimum method for ablation catheter steering, severity of cardiac condition. Specifically, image location 51 is associated with impedance, rotor cycle, severity of condition, ablation energy level and priority (order) in which it is to be ablated. Atrial tissue parameters including impedance, temperature and IECG function data are also recorded, updated and quantitatively characterized with severity and ablation sequence (the shade, color or other visual attribute in image 43 indicates high severity, abnormality, location, and ablation energy level).

Processing device 30 (e.g. a computer, controller, server) includes signal processor 15, display processor 27, severity processor 23 and repository 17. Signal processor 15 processes the acquired electrophysiological signal data to identify location of particular tissue sites of the multiple tissue locations exhibiting electrical abnormality in the acquired electrophysiological signal data and determines an area of abnormal tissue associated with individual sites of the particular sites. Processor 15 provides a visual location image map 45 in 2D or 3D (two or three dimensions) registered with cardiac locations known by ablation controller 18 and locatable by controller 18 in automatically steering an ablation catheter for ablation, for example. Image 45 identifies tissue locations to be ablated, the ablation parameters to be used for each location as well as the condition and severity of condition at each location. Ablation controller 18 uses the data associated with image 45 in automatically determining ablation pulse characteristics for use in ablating cardiac tissue at an individual site of the particular tissue sites in response to the acquired data indicating the thickness of tissue and determined area of abnormality of the individual site.

Figure 2B:
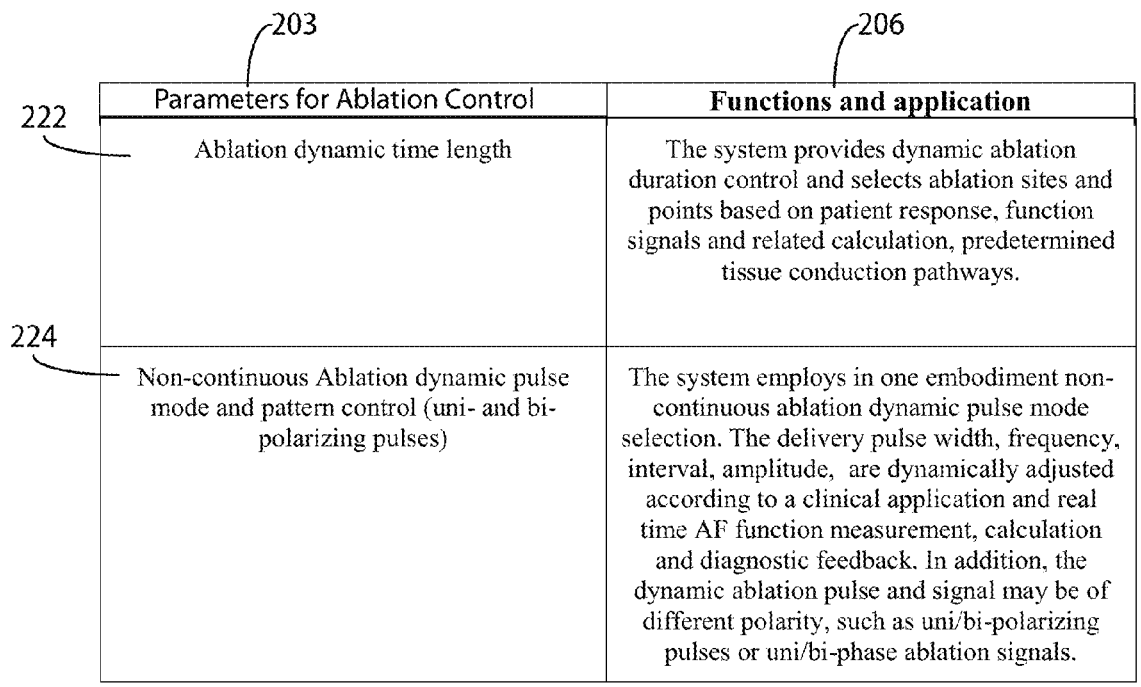

FIGS. 2A and 2B show a Table including column 203 identifying advantageous ablation control parameters 210, 212, 214, 216, 218, 220, 222 and 224 determined and used by signal processor 15. Column 206 indicates the functions of these parameters and their applications. The ablation control parameters comprise, ablation starting time (trigger and synchronizing/gating timing) T1 210, ablation frequency 212, tissue wall thickness 214, ablation effective area (dependent on catheter to tissue pressure) 216, registration and mapping of EP functions to ablation points 218, sequence and priority of tissue locations for ablation 220, ablation duration 222 and non-continuous ablation dynamic pulse pattern (using unipolar or bipolar pulses) 224. The parameters are used for ablation synchronization timing T1, for ablation energy application to atrial tissue, dynamic dominant ablation frequency selection for each ablation, tissue wall thickness selection, catheter to tissue impedance and touching force selection and selection of ablation pulse type (which is to be delivered to cardiac tissue). In another embodiment, other parameters (such as produced from ECG signals, hemodynamic signals, vital signs signals, and derived signals) are used to control an ablation procedure, ablation workflow and ablation efficiency.

FIG. 3 illustrates comparison of a known ablation procedure shown in map 303 with a system 10 procedure shown in map 306 using advantageous parameters, an ablation site priority and ablation site sequence. Shade or color (or other visual attribute) of map elements indicate severity of tissue corresponding to an element. In a known method, ablation is performed of abnormal electrophysiological (EP) sites based on EP signal acquisition and ablation convenience to eliminate one area completely and to start a next area. This may not be efficient since a multiple site abnormality may be linked electrophysiologically and functionally which means one area may not be able to be terminated completely presenting risk of over burning normal tissue and introducing an abnormality. System 10 (FIG. 1) advantageously in one embodiment analyzes the electrophysiological characteristics of multiple sites and creates an ablation priority and sequence. The ablation sequence may be an ablation site combination associated with EP signal abnormality and electrophysiological conduction and excitation propagation. In the example in FIG. 3, 11 sites are ablated in the known ablation method of map 303 in 30 minutes using 200 Watts of energy and 5 sites are ablated in the advantageous ablation method of map 306 in 10 minutes using 50 Watts of energy. In this way, the ablation completion time is reduced by 20 minutes. In map 303, there are 3 ablation sites comprising normal function tissue which do not need to be ablated. The system determines an ablation sequence and priority that is dynamically updated continuously and in real time.

Figure 4:
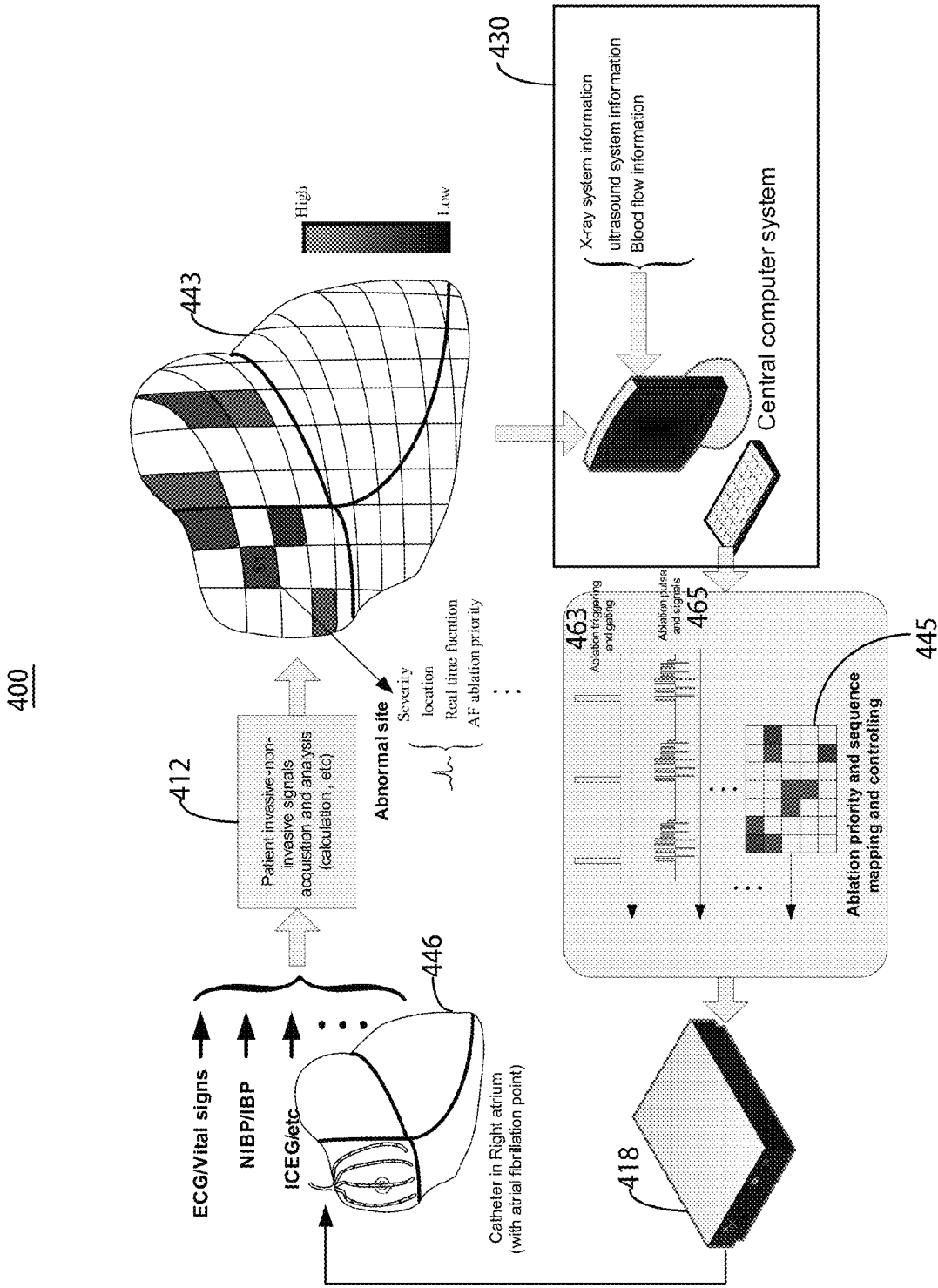
FIG. 4 shows a system for patient signal monitoring and ablation treatment using the derived parameters of the Table of FIG. 2, according to invention principles.

FIG. 4 shows system 400 for patient signal monitoring and ablation treatment using the derived parameters of the Table of FIG. 2 employing a closed loop feedback ablation and catheter steering system and dynamic continuous ablation signal adjustment. System 400 advantageously synchronizes and sequences ablation of sites and dynamically and adaptively selects ablation pulse parameters and a pulse pattern. The parameters may be derived using different patient signals and calculated data. Ablation pulse parameters and a pulse pattern are dynamically updated in response to command signals sent to an ablation controller unit. Input processor 412 continuously acquires patient signals (including ablation related intra-cardiac electrograms, surface ECG, NIBP/IBP, vital signs) from a patient and heart 446. Processor 412 acquires electrophysiological signal data from multiple tissue locations of a heart and data indicating tissue thickness at the tissue locations. The invasive and ICEG data and signals are associated (mapped) to corresponding tissue locations indicated in a predetermined anatomical 2D or 3D image 443.

Processing device 430 (e.g. a computer, controller, server) processes the acquired electrophysiological signal data, X-ray system information, or ultrasound information and blood flow information, to identify location of particular tissue sites of the multiple tissue locations exhibiting electrical abnormality in the acquired electrophysiological signal data and determines an area of abnormal tissue associated with individual sites of the particular sites. Device 430 acquires data including an anatomical image of cardiac tissue and chambers comprising an X-ray image, blood flow image or ultrasound image, for example. The composite image and function data derived using patient electrophysiological and hemodynamic signals are used by the computer to determine ablation sequence, ablation priority, ablation energy, ablation duration. For example, by using surface ECG or ICEG signals, the computer determines an ablation pulse start time and duration for each ablation. The ablation pulse width is determined and adjusted based on the real time patient signals and function changes.

Device 430 provides a visual location image map 445 in 2D or 3D (two or three dimensions) registered with cardiac locations known by ablation controller 418 and locatable by controller 418 in automatically steering an ablation catheter for ablation, for example. Device 430 generates an ablation trigger, gating and synchronization signal 463 to start ablation and selects an ablation pulse pattern and pulse characteristics 465. Image 445 identifies tissue locations to be ablated, the ablation parameters to be used for each location as well as the condition and severity of condition at each location. Ablation controller 418 uses the data associated with image 445, synchronization signal 463 and pulse characteristics 465 in ablating cardiac tissue at an individual site of the particular tissue sites in response to the acquired data indicating the thickness of tissue and determined area of abnormality of the individual site.

Device 430 determines real time mapping and registration, optimum appropriate ablation time, ablation pulse width and rate, ablation delivery location and ablation energy. In addition, the ablation duration, frequency range (band and dominant frequency) and catheter movement information (moving to an optimum ablation location and movement speed) for each ablation point are provided to a physician and used in control of the ablation procedure. Multiple methods may be used to provide image 445 and data representation, such as by using a fuzzy system or expert system, for example.

Figure 5:
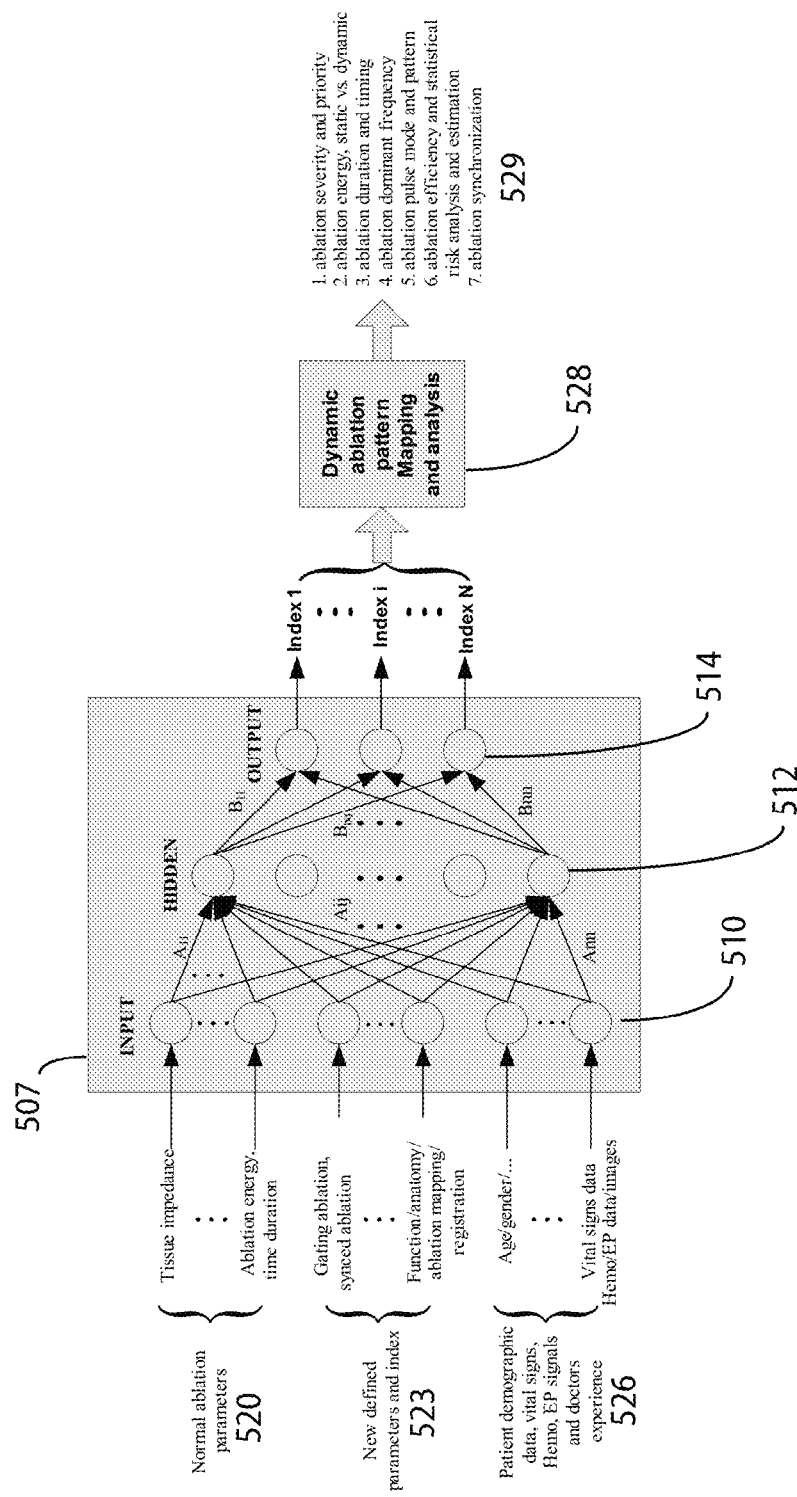
FIG. 5 shows a cardiac ablation device controller using an artificial neural network (ANN), according to invention principles.

FIG. 5 shows a cardiac ablation device controller and multi ablation parameter based decision system using an artificial neural network (ANN) 507. The ANN calculation and decision module 507 has self-learning ability involving processing training data. The ANN based control of ablation signals uses patient signal analysis results, patient history and physician experience (input and suggested control mode) to provide quantitative and qualitative control and adjustment of an ablation device. ANN unit 507 derives detailed ablation parameters for ablation control of ablation synchronization, ablation pulse width, ablation priority and severity and ablation site location.

ANN unit 507 combines and maps input parameters 520, 523 and 526, to parameters processed by calculation unit 528 that provides output parameters 529. The output parameters 529 indicate ablation site position, type, severity and relative priority for treatment, ablation energy, ablation duration, timing and dominant frequency, ablation pulse type and pattern, ablation efficiency and risk and synchronization. ANN unit 507 structure comprises 3 layers, an input layer 510, hidden layer 512 and output layer 514. ANN unit $A_{ij}$ weights are applied between input layer 510 and hidden layer 512 components of the ANN computation and $B_{pq}$ weights are applied between hidden layer 512 and calculation components 514 of the ANN computation. The $A_{ij}$ weights and $B_{pq}$ weights are adaptively adjusted and tuned using a training data set.

Figure 6:
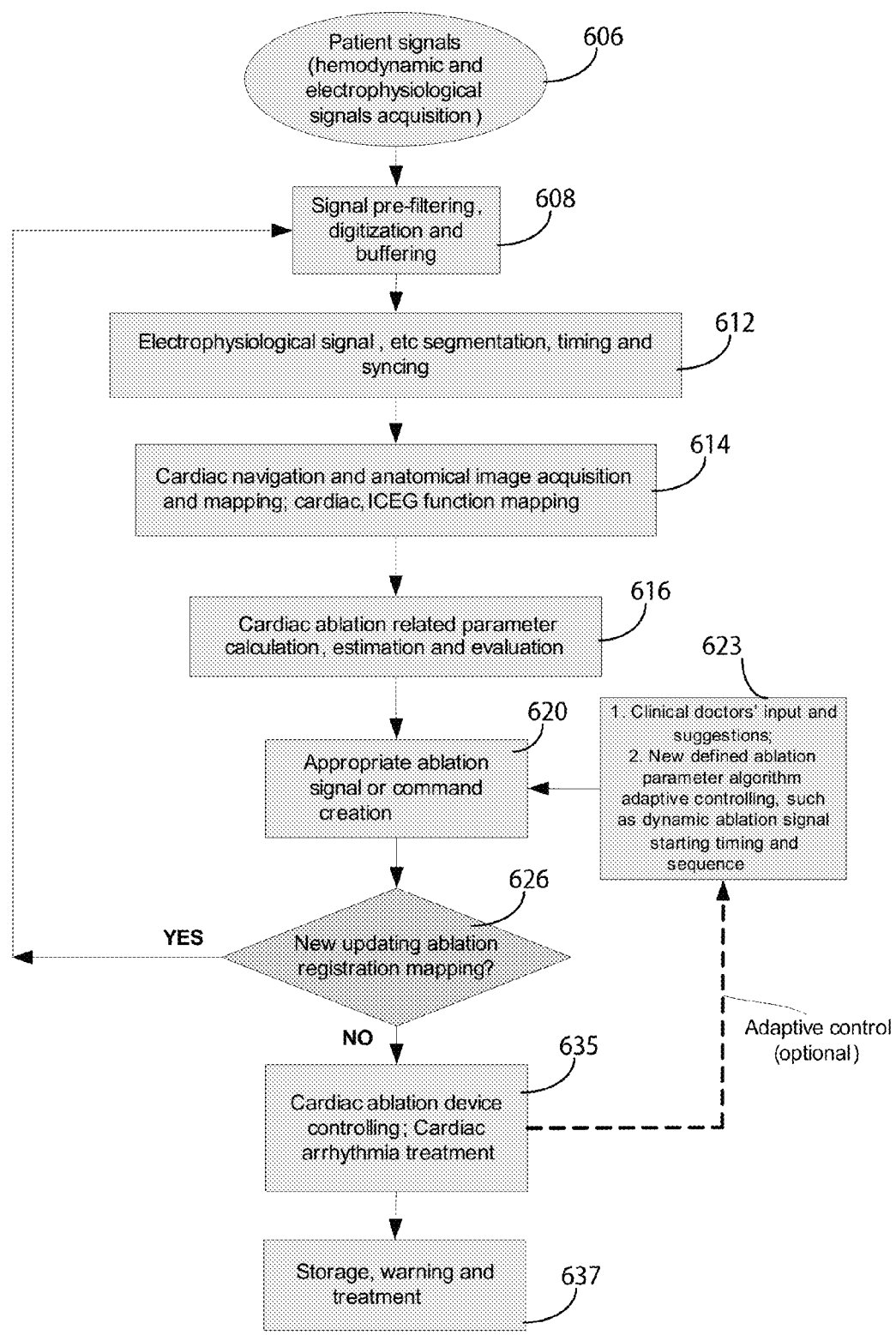
FIG. 6 shows a flowchart of a method for adaptive cardiac ablation control, according to invention principles.

FIG. 6 shows a flowchart of a method for adaptive cardiac ablation control used by system 10 (FIG. 1). Input processor 12 buffers, filters (to remove power line noise, patient movement and respiration noise) and digitizes an ECG signal, ICEG signal, invasive and non-invasive blood pressure signals, respiration signals, SPO2 signals and vital signs signals in step 608 received from a patient in step 606. Processor 15 in step 608 filters the received signal data using a filter adaptively selected in response to data indicating clinical application, to remove patient movement and respiratory artifacts as well as power line noise. In step 612, processor 15 detects patient signal parameters and segments an ECG signal into sections including, P wave, Q wave, R wave, S wave, T wave, U wave portions and determines peak timing and end-of-diastolic (EoD) and end-of-systolic (EoS) points.

The P wave, Q wave, R wave, S wave, T wave, U wave portions and points of the received ECG signal are identified by detecting peaks within the received ECG data using a known peak detector and by segmenting the ECG signal into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

In step 614, processor 15 performs anatomical navigation of a catheter for image acquisition and ECG, ICEG and EP signal acquisition and mapping to, (and association with), cardiac tissue locations on an X-ray image, ultrasound image or other cardiac image, for example. Signal processor 15 in step 616 performs ablation related parameter calculation and selection including deriving appropriate ablation control signals, an ablation site sequence, selection of ablation pulse type and pattern, a dynamic ablation frequency range and real time feedback controlled ablation energy using a lookup table as in FIG. 2. Processor 15 in step 620 generates ablation control signals for adaptive ablation and treatment of a patient.

If signal processor 15 in step 626, determines a new ablation process is to be performed using an updated ablation mapping of tissue sites to be ablated, the process is repeated from step 608. If a new ablation process is not to be performed, processor 15 in step 635 performs adaptive ablation and treatment of a patient, using the generated parameters and control signals and closed loop ablation system control. The system employs dynamic real time ablation registration of sites with an image map and adaptive update of ablation site sequence, priority, location and applied energy. In step 637 processor 15 stores data representing the ablation parameters used for ablation in repository 17. Processor 15 in step 623 adaptively adjusts ablation parameters and a control method in response to user input and tissue site severity and current ablation treatment and control parameters.

FIGS. 7a and 7b show a multi-functional ablation registration map and an associated ablation pulse sequence illustrating ablation mapping and anatomical and ICEG signal function registration. The ablation registration map 703 shows ablation priority and sequence for left atrial chamber 705 with ablation triggered in response to a surface ECG or an IECG signal. Processor 15 provides a treatment suggestion and analysis 707 based on the mapping 703. The ablation pulse duration for each ablation is controlled and gated by the surface ECG or IECG signal. Multi-functional ablation registration map 703 shows three significant abnormal rotor areas in a left atrial chamber. In order to achieve the best ablation result (ablation time and low energy burning), a P wave 712 (derived from Surface ECG signal 710) pulse is used as a gating window for ablation signal duration control for each ablation site 714.

System 10 (FIG. 1) generates ablation control signals in response to advantageous parameters including ablation sequence, ablation gating, ablation time duration, ablation dominant frequency and ablation pulse pattern and processor 15 superimposes the parameter data on associated locations on an anatomical image. The data superimposed includes ICEG signal function data (amplitude, dominant frequency component, energy, complexity). There are 3 abnormal atrial fibrillation rotors in the ablation mapping. Processor 15 determines from site ICEG signals an ablation sequence for the ablation procedure comprising, site 1, then site 2 and then site 3. The ablation sequence is an adaptive procedure and after each ablation, the site registration mapping is updated to guide a user for optimized ablation. Ablation for each site is non-continuous ablation and an ablation process is segmented into portions and is synchronized by signal 712 so time duration of each ablation occurs within one heart cycle. The ablation time for each site depends on the severity and abnormality of the AF rotors. For example, in this case, site 1 needs ablation twice while site 2 needs once and site 3 need 3 times (where 1 time=pulse duration t, 2 times=2t and so on). The ablation for each site depends on local cardiac tissue properties (such as tissue wall thickness, electrophysiological characteristics). In this example, the ablation time durations for the sites are: 0.5, 0.4, 0.8 seconds respectively. In order to achieve the best ablation results, the ablation signal mode and dominant frequency may need to be varied. In this example, for site 1, a uniphasic ablation pulse with dominant frequency around 474 K Hz is used. Site 2 and site 3 use uniphasic and biphasic separation with dominant frequency focusing on 450K Hz and 500 K Hz.

The system determines priority of ablation of tissue site based on severity of abnormality of the tissue sites (the higher the severity the higher the priority and order in which the site is ablated). The severity is determined from distortion of a P wave of the electrophysiological signal at the site (e.g. acquired using a basket catheter). The distortion is derived based on measurement of P wave peak amplitude, peak amplitude variation, peak timing latency i.e. timing shift and dominant frequency change. Patient ablation and treatment varies based on patient gender, age, demographic data, health status, prior cardiac treatment (e.g. surgery) and medication. For the example in FIG. 7, cardiac patient parameters and characteristics employed to determine ablation treatment include ablation time, ablation duration, ablation frequency, ablation energy and ablation pulse type. Other parameters may be used for ablation parameter determination and dynamic adjustment of treatment and surgery, such as tissue wall thickness, P wave amplitude, P wave total energy, frequency ratio, P wave time-frequency distribution and clinical procedure type.

FIGS. 8, 9 and 10 present lookup tables showing tissue abnormality and rotor characteristics and associated ablation control parameters. Table 803 (FIG. 8) associates a size range of an abnormal tissue area showing Atrial Fibrillation (column 805) with a tissue thickness range (column 807), number of ablation pulses of a fixed width that are separated or combined into an extended pulse width (column 809) and with an ablation time duration (column 811). The larger the abnormality tissue area size and the greater the severity of the abnormality, the more ablation pulses and energy ablation duration is applied. Table 823 (FIG. 9) associates an Atrial Fibrillation rotor dominant frequency range (column 825) with an ablation frequency (column 827). Processor 15 identifies a dominant frequency in a P wave acquired from an abnormal tissue site of a patient and uses Table 823 to determine a corresponding ablation frequency to terminate fibrillation. An ablation frequency is adaptively selected for each patient.

Table 843 (FIG. 10) shows AF rotor entry characteristics used by processor 15 for determining an ablation pulse to be used for each identified abnormal area. Table 843 associates Atrial Fibrillation rotor characteristics, e.g., type of rotor such as single phase, biphase (column 845) with type of ablation pulse used, e.g. uniphase, biphase (column 847). If an AF rotor is complicated in phase and shape, a multi-phasic ablation pulse pattern is used for treatment of AF.

Figure 11:
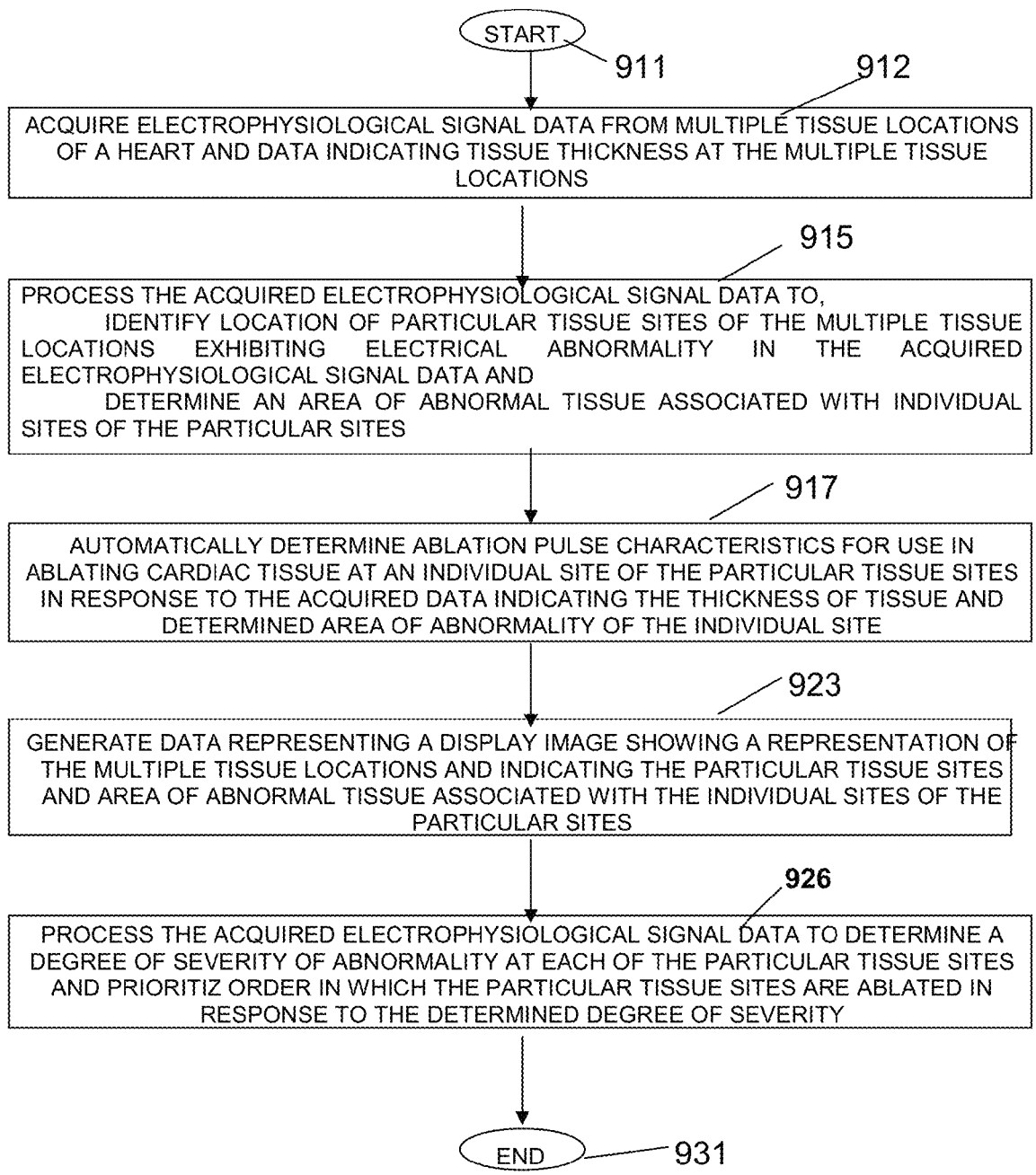
FIG. 11 shows a flowchart of a process used by a system for heart ablation unit control, according to invention principles.

FIG. 11 shows a flowchart of a process used by system 10 (FIG. 1) for heart ablation unit control. In step 912 following the start at step 911, input processor 20 acquires electrophysiological signal data from multiple tissue locations of a heart, data indicating tissue thickness at the multiple tissue locations and data indicating a measured dominant rotor frequency at an individual site. In step 915 signal processor 15 processes the acquired electrophysiological signal data to, identify location of particular tissue sites of the multiple tissue locations exhibiting electrical abnormality indicated by the acquired electrophysiological signal data and determines an area of abnormal tissue associated with individual sites of the particular sites. Ablation controller 18 in step 917 automatically determines ablation pulse characteristics for use in ablating cardiac tissue at an individual site of the particular tissue sites in response to the acquired data indicating the thickness of tissue and determined area of abnormality of the individual site.

Ablation controller 18 determines an ablation pulse characteristic comprising an ablation pulse frequency in response to the rotor frequency by selection of the pulse frequency from predetermined information associating ablation pulse frequency with rotor frequency for a patient having similar patient demographic characteristics as the patient. The demographic characteristics comprise at least one of, age, weight, gender, body mass index and height. Ablation controller 18 determines an ablation pulse characteristic comprising pulse width in response to at least one, (a) the thickness of tissue and (b) the determined area of abnormality, by selection of the pulse width from predetermined information associating ablation pulse width with thickness of tissue and area of tissue for a patient having similar patient demographic characteristics as the patient. Ablation controller 18 determines an ablation pulse characteristic comprising pulse electrical energy in response to at least one, (a) the thickness of tissue and (b) the determined area of abnormality by selection of the pulse electrical energy from predetermined information associating ablation pulse electrical energy with tissue thickness and abnormality area for a patient having similar patient demographic characteristics as the patient. Ablation controller 18 also determines an ablation pulse characteristic comprising pulse type by selecting pulse type from, (a) a uniphase type and (a) biphase type in response to a determined rotor signal type. The ablation controller automatically re-determines and updates the ablation pulse characteristics in response to performing ablation at the individual site and synchronizes ablation pulse delivery with a heart cycle synchronization signal. Ablation controller 18 compares areas of abnormality after ablation of the individual site with areas of abnormality prior to ablation of the individual site and indicates differences and adaptively alters the selection of ablation sites and ablation characteristics in response to the differences.

In step 923, display processor 27 generates data representing a display image showing a representation of the multiple tissue locations and indicating the particular tissue sites and area of abnormal tissue associated with the individual sites of the particular sites. The representation of the multiple tissue locations comprises a two dimensional (2D) or three dimensional (3D) representation of a patient heart. Display processor 23 automatically updates the display image to show an updated area of abnormal tissue associated with the individual sites in response to performing ablation at the individual site. Severity processor 23 in step 926 processes the acquired electrophysiological signal data to determine a degree of severity of abnormality at each of the particular tissue sites and prioritize order in which the particular tissue sites are ablated in response to the determined degree of severity. Severity processor 23 processes the acquired electrophysiological signal data to determine the degree of severity of abnormality by determining a measure of distortion in a P wave in the electrophysiological signal data in response to at least one of, (a) change in peak amplitude of the P wave, (b) change in dominant frequency of the P wave, (c) change in energy of the P wave and (d) change in time duration between successive peaks of the P wave. The process of FIG. 11 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system detects and characterizes atrial signals (e.g. ECG signals) in response to an atrial gating signal derived from a P wave signal or atrial function portion and identifies and maps signal waveform changes to anatomical cardiac tissue in characterizing atrial multi-rotor (multi-excitation) signal patterns for determining ablation treatment parameters. Further, the processes and applications may, in alternative embodiments, be located on one or more (e.g., distributed) processing devices on a network linking the units FIG. 1. Any of the functions and steps provided in FIGS. 1-11 may be implemented in hardware, software or a combination of both. No claim element herein is to be construed under the provisions of 35 U.S.C. 112, sixth paragraph, unless the element is expressly recited using the phrase "means for."

What is claimed is:

1. A system for heart ablation unit control, comprising:
   an input processor for acquiring electrophysiological signal data from a plurality of tissue locations of a heart and data indicating tissue thickness at said plurality of tissue locations;
   a signal processor for processing the acquired electrophysiological signal data to,
       identify location of particular tissue sites of said plurality of tissue locations exhibiting electrical abnormality in said acquired electrophysiological signal data and
       determine an area of abnormal tissue associated with individual sites of said particular sites;
   an ablation controller for automatically determining ablation pulse characteristics for use in ablating cardiac tissue at an individual site of said particular tissue sites in response to the acquired data indicating the thickness of tissue and determined area of abnormality of the individual site; and
   a severity processor for processing the acquired electrophysiological signal data to determine a degree of severity of abnormality at each of said particular tissue sites and prioritizing order in which said particular tissue sites are ablated in response to the determined degree of severity, wherein said severity processor processes the acquired electrophysiological signal data to determine said degree of severity of abnormality by determining a measure of distortion in a P wave in said electrophysiological signal data in response to at least one of, (a) change in peak amplitude of said P wave, (b) change in dominant frequency of said P wave, (c) change in energy of said P wave and (d) change in time duration between successive peaks of said P wave.

2. The system according to claim 1, including
a display processor for generating data representing a display image showing a representation of said plurality of tissue locations and indicating said particular tissue sites and area of abnormal tissue associated with said individual sites of said particular sites.

3. The system according to claim 2, wherein
said representation of said plurality of tissue locations comprises a two dimensional (2D) or three dimensional (3D) representation of a patient heart.

4. The system according to claim 1, wherein
said input processor acquires data indicating a measured dominant rotor frequency at said individual site and said ablation controller determines an ablation pulse characteristic comprising pulse frequency in response to the rotor frequency.

5. The system according to claim 1, wherein
said input processor acquires data indicating a measured dominant rotor frequency at said individual site and said ablation controller determines an ablation pulse characteristic comprising an ablation pulse frequency in response to the rotor frequency by selection of said pulse frequency from predetermined information associating ablation pulse frequency with rotor frequency for a patient having similar patient demographic characteristics as said patient.

6. The system according to claim 5, wherein
said demographic characteristics comprise at least one of, age, weight, gender, body mass index and height.

7. The system according to claim 1, wherein
said ablation controller determines an ablation pulse characteristic comprising pulse width in response to at least one, (a) of said thickness of tissue and (b) said determined area of abnormality by selection of said pulse width from predetermined information associating ablation pulse width with thickness of tissue and area of tissue for a patient having similar patient demographic characteristics as said patient.

8. The system according to claim 7, wherein
said ablation controller determines an ablation pulse characteristic comprising pulse electrical energy in response to at least one, (a) of said thickness of tissue and (b) said determined area of abnormality by selection of said pulse electrical energy from predetermined information associating ablation pulse electrical energy with tissue thickness and abnormality area for a patient having similar patient demographic characteristics as said patient.

9. The system according to claim 1 including
a display processor for generating data representing a display image showing a representation of said plurality of tissue locations and indicating said particular tissue sites and area of abnormal tissue associated with said individual sites of said particular sites and the priority of order of ablation of said particular tissue sites.

10. The system according to claim 9, wherein
said display processor automatically updates said display image to show an updated area of abnormal tissue associated with said individual sites in response to performing ablation at said individual site.

11. The system according to claim 9, wherein
said ablation controller automatically re-determines and updates said ablation pulse characteristics in response to performing ablation at said individual site.

12. The system according to claim 1, including
a display processor for generating data representing a display image showing a representation of said plurality of tissue locations and indicating said particular tissue sites and area of abnormal tissue associated with said individual sites of said particular sites and the priority of order of ablation of said particular tissue sites and
said display processor updates said display image to show an updated area of abnormal tissue associated with said individual sites in response to performing ablation at said individual site.

13. The system according to claim 1, wherein
said ablation controller determines an ablation pulse characteristic comprising pulse type by selecting pulse type from, (a) a uniphase type and (a) biphase type in response to a determined rotor signal type.

14. The system according to claim 1, wherein
said ablation controller determines an ablation characteristics comprising interval between ablation episodes and ablation duration in response to at least one, (a) of said thickness of tissue and (b) said determined area of abnormality by selection of said pulse width from predetermined information associating ablation pulse width with thickness of tissue and area of tissue for a patient having similar patient demographic characteristics as said patient.

15. The system according to claim 1, wherein
said ablation controller synchronizes ablation pulse delivery with a heart cycle synchronization signal.

16. The system according to claim 1, wherein
said ablation controller compares areas of abnormality after ablation of said individual site with areas of abnormality prior to ablation of said individual site and indicates differences.

17. A method for heart ablation unit control, comprising the activities of:
acquiring electrophysiological signal data from a plurality of tissue locations of a heart and data indicating tissue thickness at said plurality of tissue locations;
processing the acquired electrophysiological signal data to,
identify location of particular tissue sites of said plurality of tissue locations exhibiting electrical abnormality in said acquired electrophysiological signal data and
determine an area of abnormal tissue associated with individual sites of said particular sites;
acquiring data indicating a measured dominant rotor frequency at said individual site;
automatically determining ablation pulse characteristics comprising pulse frequency in response to the rotor frequency for use in ablating cardiac tissue at an individual site of said particular tissue sites in response to the acquired data indicating the thickness of tissue and determined area of abnormality of the individual site.

18. The method according to claim 17, including the activity of
generating data representing a display image showing a representation of said plurality of tissue locations and indicating said particular tissue sites and area of abnormal tissue associated with said individual sites of said particular sites.

19. The method according to claim 18, wherein
said representation of said plurality of tissue locations comprises a two dimensional (2D) or three dimensional (3D) representation of a patient heart.

20. The system according to claim 17, including the activity of
processing the acquired electrophysiological signal data to determine a degree of severity of abnormality at each of said particular tissue sites and prioritizing order in which said particular tissue sites are ablated in response to the determined degree of severity.

21. A system for heart ablation unit control, comprising:
an input processor for acquiring electrophysiological signal data from a plurality of tissue locations of a heart and data indicating tissue thickness at said plurality of tissue locations;
a signal processor for processing the acquired electrophysiological signal data to,
identify location of particular tissue sites of said plurality of tissue locations exhibiting electrical abnormality in said acquired electrophysiological signal data and
determine an area of abnormal tissue associated with individual sites of said particular sites, wherein said input processor acquires data indicating a measured dominant rotor frequency at said individual site; and
an ablation controller for automatically determining ablation pulse characteristics comprising pulse frequency in response to the rotor frequency for use in ablating cardiac tissue at an individual site of said particular tissue sites in response to the acquired data indicating the thickness of tissue and determined area of abnormality of the individual site.

22. The system according to claim 21, wherein
said input processor acquires said data indicating a measured dominant rotor frequency at said individual site and said ablation controller determines said ablation pulse characteristic comprising said ablation pulse frequency in response to the rotor frequency by selection of said pulse frequency from predetermined information associating ablation pulse frequency with rotor frequency for a patient having similar patient demographic characteristics as said patient.

23. The system according to claim 22, wherein
said demographic characteristics comprise at least one of,
age, weight, gender, body mass index and height.

\* \* \* \* \*